United States Patent [19]

Henry

[11] Patent Number: 5,589,156
[45] Date of Patent: Dec. 31, 1996

[54] PRILOCAINE AND HYDROFLUOUROCARBON AEROSOL PREPARATIONS

[76] Inventor: Richard A. Henry, 7 Toronto Street, Kingston, Ontario, Canada, K7L 4A3

[21] Appl. No.: 435,812

[22] Filed: May 5, 1995

Related U.S. Application Data

[63] Continuation-in-part of Ser. No. 408,877, Mar. 24, 1995, and Ser. No. 236,408, May 2, 1994, Pat. No. 5,453,445, and Ser. No. 405,930, Mar. 17, 1995.

[51] Int. Cl.$^6$ ........................................ A61K 9/12
[52] U.S. Cl. .................. 424/45; 424/46; 424/47; 514/818; 514/974
[58] Field of Search ................... 424/45, 47, 46; 514/818, 974

[56] References Cited

U.S. PATENT DOCUMENTS

| | | | |
|---|---|---|---|
| 5,118,494 | 6/1992 | Schultz et al. | 424/45 |
| 5,190,029 | 3/1993 | Byron et al. | 424/45 |
| 5,225,183 | 6/1993 | Purewal et al. | 424/45 |
| 5,276,032 | 1/1994 | King et al. | 514/239.2 |
| 5,380,754 | 1/1995 | Miller et al. | 514/513 |

FOREIGN PATENT DOCUMENTS

| | | | |
|---|---|---|---|
| 07333 | 7/1990 | WIPO | 424/45 |
| 14466 | 9/1992 | WIPO | 424/45 |

OTHER PUBLICATIONS

Morén, F. et al. (1993). Aerosols in Medicine. Principles, Diagnosis and Therapy. Elsevier Sci. Publishers, pp. 303–319.

Madar, M. J. (1993). J. Appl. Physiology 74(3): 1419–1424.

"Neural blockade in Clinical Anesthesia and Management of Pain" 2nd Edition. Chapters 1 and 2. Edited by Michael J. Cousins and Phillip O. Bridenbaugh. Published by Lippencott. (1989).

*Primary Examiner*—Raj Bawa
*Attorney, Agent, or Firm*—Whitham, Curtis, Whitham & McGinn

[57] ABSTRACT

Aerosol compositions used for anesthetizing mammals in both human and veterinary applications include prilocaine base solubilized in the hydrofluorocarbon (HFC) propellants 1,1,1,2-tetrafluoroethane and 1,1,1,2,3,3,3-heptafluoropropane. Prilocaine base has been found to be readily soluble in HFC propellants when combined in liquid or micro rod form, and a solution stable to temperatures as low as $-82°$ C. is formed upon combination of the two components. In the aerosol compositions, the HFCs are the only propellants used. Additional pharmaceutical constituents can also be combined the the prilocaine base/HFC composition to provide a multi-component anesthetic, and it has been found that the presence of prilocaine in the combination can assist in solubilizing and/or suspending these pharmaceutical constituents. Some example pharmaceutical compositions within the practice of this invention include HFC, prilocaine base, and a pharmaceutical other prilocaine selected from the group consisting of bronchodilators, antiinflammatories, antitusives, vasoactive drugs, vasoconstrictors, antibiotics, peptides, steroids, enzymes, antihistamines, hormones, enzyme and receptor inhibitors and agonists, 5-aminolevulinic acid, antiseptics, disinfectants, procaine, cocaine, chloroprocaine, tetractaine, mepivacaine, lidocaine, bupivacaine, etidocaine, ropivacaine, benzocaine, and phenylephrine.

29 Claims, No Drawings

PRILOCAINE AND HYDROFLUOUROCARBON AEROSOL PREPARATIONS

CROSS-REFERENCE TO RELATED APPLICATIONS

This application is a continuation-in-part application of the co-pending patent application filed Mar. 24, 1995, having U.S. Ser. No. 08/408,877, and the patent application filed May 2, 1994, having U.S. Ser. No. 08/236,408, now U.S. Pat. No. 5,453,445, and the co-pending patent application filed Mar. 17, 1995, having U.S. Ser. No. 08/405,930, and the complete contents of these three patent applications are herein incorporated by reference.

DESCRIPTION

BACKGROUND OF THE INVENTION

1. Field of the Invention

The invention is generally related to aerosol formulations which include hydrofluoride propellants and prilocaine base.

2. Description of the Prior Art

Prilocaine is a local anesthetic drug which has the chemical formula:

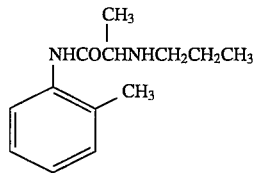

Prilocaine is described in British Patent 839,943 (1960 to Astra), and takes the form of crystalline needles having a melting point of 37°–38° C. The hydrochloride salt, having the formula $C_{13}H_{21}ClN_2O$, is crystallized from ethanol and isopropyl ether, and is readily soluble in water.

Local anesthetic drugs block nerve impulses by interfering with the opening of voltage gated sodium channels of excitable membranes, such as neuronal cell membranes. When enough channels are blocked, neuronal conduction is terminated within the anesthetized portion of the particular nerve axon. This mechanism of pain relief is quite different from those used by analgesic agents.

The potency of anesthetics in clinical situations depends on both the ability to reach the nerve fibers and their intrinsic blocking activities. Factors such as nerve sheath penetration, vascular absorption, and local tissue binding are all important determinants of functional potency. In addition, volume, pH, and buffering capacity of the injected anesthetic solution are important.

Local anesthetics are traditionally injected into the desired site of action by the use of a needle and syringe. Most formulations of local anesthetics are aqueous solutions of the hydrochloride salt forms of the drug in 0.5–2% weight/volume concentrations. These solutions are designed for injection either diffusely into tissue, around nerves, or into the intrathecal or epidural spaces.

The delivery of local anesthetic agents to skin wounds remains a problem and is largely still achieved by injection of the aqueous local anesthetic around or into the wound. This treatment mechanism can be disadvantageous because the needle itself causes pain on penetration, and, the volume of anesthetic solution can cause stretching at the site, which also causes pain. Furthermore, preservatives such as parabens, ethyl alcohol, cetylpyridinium chloride, benzalkonium chloride, and the like, which may be used in the aqueous solution can cause stinging at the wound site.

A topical formulation of 0.5% tetracaine hydrochloride, epinephrine 1:2000, and 11.8% cocaine hydrocloride, is described in *Handbook of Pediatric Emergencies*, 1994, Ed. Baldwin, Little, Brown and Company. This formulation is applied by holding a cotton ball soaked in the solution for a period of 10–15 minutes. This treatment scheme and formulation suffers from the slow absorption of the salt form of the local anesthetic which requires that the solution be held in place for long periods of time, the use of cotton balls directly on the wound site, and the requirement of cleaning the wound prior to application of the formulation. In addition, in order to obtain deep blocking, the treatment scheme must be supplemented with injection of a local anesthetic formulation.

Topical anesthesia requires rapid absorption of drug in order to block nerve conduction. Topically applied gels and fluids have not proven successful in many environments. For example, intraurethrally delivered lidocaine gel was shown to be no more effective than plain lubricant jelly during cystoscopy (see, Stein et al., *Journal of Urology*, June 1994, Vol. 151, pages 1518–1521).

Lidocaine has been delivered in aerosol form to the mucous membranes of the airway using nebulized aqueous preparations of the lidocaine hydrochloride salt and using metered dose inhaler (MDI) formulations with chlorofluorocarbon (CFC) propellants and solubilizing and/or dispersing agents. However, experience has shown that these formulations suffer from large droplet formation which prevents satisfactory inhalable or indirect delivery to the upper airway, including the larynx and trachea. In addition, the requirement of organic solvents and adjuvants in the aerosol formulations limits the concentration of the active medicament, and thus limits the dispensable dose. Moreover, these formulations have not been used topically and would not be successful in topical application because the adjuvants and solvents are themselves irritants which would cause pain when administered to sensitive mucous membranes and wounds.

Chlorofluorocarbon (CFC) propellants have been widely used in aerosol formulations; however, CFC propellants are being phased out under international treaties due to their possible adverse impact on the ozone layer. Hydrofluorocarbon (HFC) propellants have been investigated extensively as substitutes for CFCs. While chemically similar to to CFCs, HFCs have some property differences that have made formulating certain products very difficult, and particularly formulating medical and pharmaceutical aerosols wherein the ability to provide a controlled amount of drug and, in some instances, particles or droplets of respirable size (e.g., less than 10 μm), is extremely important.

SUMMARY OF THE INVENTION

An object of this invention is to provide novel aerosol formulations which include prilocaine, with or without additional medicaments, in HFC propellants, without additional organic solvents and surfactants.

Another object of this invention is to provide a method of using prilocaine as a solubilizing agent in HFC propellants.

Another object of this invention is to provide a new composition of prilocaine wherein prilocaine, in liquid or amorphous form, is associated with an HFC propellant.

According to the invention, prilocaine in base form has been found to be soluble in the HFC propellants 1,1,1,2-tetrafluoroethane and 1,1,1,2,3,3,3-heptafluoropropane. Prilocaine is soluble when combined with the HFC propellant in liquid form, but is not soluble when combined with the HFC propellant in its crystalline form. The combination of prilocaine base in liquid form and HFC propellant forms a stable liquid solution having an oily consistency. When prilocaine base in liquid form is mixed with the HFC propellant it is thought to form a 1:1 molecular ionic complex that keeps the prilocaine in solution and alters the solubility of this complexed mixture such that it is completely miscible or soluble in prilocaine. The prilocaine complexed HFC propellant has altered physical characteristics with improved solubility, improved suspension characteristics, a low vapor pressure and higher viscosity. The association or complex between prilocaine and HFC propellants is disrupted by the presence of water or ethanol resulting in the release of the HFC propellant. Prilocaine liquid can be combined with other medicaments, and particularly other anesthetics, and serve as a solubilizing agent by improving the solubility characteristics of the HFC propellant such that the added local anesthetic forms a stable solution in the prilocaine/HFC solution complex. The oily character of the prilocaine liquid/HFC complex may serve as a valve lubricating aid when dispensing the aerosol formulation from an MDI; thereby, overcoming or obviating the conventional formulations which need additional valve lubricants. The prilocaine liquid/HFC complex also allows the creation of stable suspensions of certain particulate medicaments (e.g., beta-agonists such as albuterol, etc.). The liquid character of the prilocaine/HFC complex may be advantageous in topical treatment methodologies since the prilocaine can be sprayed onto a site to coat the site with a liquid, as opposed to a fine powder, which will be more rapidly absorbed due to the liquid character of the prilocaine, the fact that the prilocaine is present as a lipid-soluble base, and the rapid departure of the complexed HFC propellant from the interaction of the complex with water on the membrane and skin surfaces of the patient.

DETAILED DESCRIPTION OF THE PREFERRED EMBODIMENTS OF THE INVENTION

Liquid prilocaine base can be made by suspending prilocaine hydrochloride in ethyl acetate and washing with a suitable aqueous base, such as sodium bicarbonate, until all the solid is consumed. The ethyl acetate can be removed using standard rotary evaporation or other procedures. After removal of ethyl acetate, the prilocaine base residue is then dissolved in a lower boiling point solvent, such as dichloromethane, to remove the ethyl acetate by azeotropic distillation. The dichloromethane is then evaporated off using a rotary evaporator, and the prilocaine base is dried under high vacuum.

The prilocaine base obtained by the above procedure was a liquid at room temperature, but was easily converted to its usual crystalline needle form by cooling or by the addition of crystal seeds to the liquid. As noted above, prilocaine is ordinarily a solid at room temperature which has the form of crystalline needles that melt at 38° C. However, the processing conditions used formed a liquid prilocaine base below its normal melting point. This is not an unusual occurrence where a low melting point solid is found to remain in liquid form below its melting point; however, this property in prilocaine base has been heretofor unknown. Further cooling or the addition of crystal seeds crystallizes these substances and they remain in solid form up to their predicted melting point.

A reference standard prilocaine base sample obtained from the Astra Pharmaceutical Company of Sweden was used to verify the nature and purity of the liquid prilocaine base as described above. It was confirmed using thin layer chromatography on silica gel, infra-red (IR) spectrometry, and nuclear magnetic resonance (NMR) imaging that the liquid prilocaine base was the same as the standard prilocaine base.

It has been discovered that the liquid prilocaine base can be readily solubilized or absorbed into HFC propellants 1,1,1,2-tetrafluoroethane and 1,1,1,2,3,3,3-heptafluoropropane. The combination of liquid prilocaine base and the HFC propellant forms a stable oily liquid.

By contrast, prilocaine base in its ordinary crystalline needle form is not soluble in HFC propellants. The crystal structure is thought to prevent the polar/ionic interaction of prilocaine and HFC propellant and the crystals remain insoluble.

When the crystalline needles are melted by heating to a temperature above 38° C., the liquid was found to be readily solubilized and absorbed in the HFC propellants to form a stable oily liquid. As long as no needle crystals are present, the prilocaine base/HFC combination remains stable when cooled down to −82° C.; however, seeding the solution with needles will cause dissolution of the prilocaine base/HFC combination.

In addition to liquid prilocaine base being found to be soluble in HFCs, it has been found that prilocedne base in micro rod crystal form, as opposed to the usual needle form, is soluble in HFC propellants. Micro rods of prilocaine base may be obtained using precipitation and filtering from a super-saturated solution. The Reference Standard Sample of prilocaine base from Astra Pharmaceuticals was provided in micro rod crystal form. The micro rods are identical to the crystalline needles of prilocaine base chemically, but not physically.

An important feature of this invention is that prilocaine base be used in liquid form or micro-rod form when making aerosol formulations with HFC propellants. Combining liquid or micro-rod prilocaine base with HFC propellants produces a stable complex or association that has the form of an oily liquid solution which can be used in MDIs or other formulations. The solution is ideal for topical delivery to a wound site or the like, in that the prilocaine base is applied as a liquid and is absorbed quickly, absorption is enhanced by the prilocaine being present in its lipid soluble base form, and the complexed HFC propellant quickly dissociates from the prilocaine upon contact with water and other contaminants at the site. The rapid absorption allows for quick and effective local anesthesia without causing pain or discomfort on application. Because the prilocaine base is in liquid form as it is sprayed, it has the utility of forming a thin film coating on any site needing to be anesthetized. Such sites include the mucous membranes of the airway, gastrointestinal tract and genito-urinary tract, and all wound surfaces where the epidermis is comprimised to allow rapid absorption of topical local anesthetic as well as internal organ surfaces exposed during surgical procedures. The oily character of the liquid improves asorption to the applied surface while remaining easy to wash or wipe off.

Example 1 describes the formation of the complex of liquid prilocaine base and HFC propellants.

EXAMPLE 1

Liquid prilocaine base, provided as an oily liquid without any crystal seeds, is readily miscible with the hydrofluorocarbon propellants 1,1,1,2-tetrafluoroethane (HFC-134a) and 1,1,1,2,3,3,3-heptafluoropropane (HFC-227). Likewise, prilocaine base in micro rod crystalline form is readily miscible with the hydrofluorocarbon propellants 1,1,1,2-tetrafluoroethane (HFC-134a) and 1,1,1,2,3,3,3-heptafluoropropane (HFC-227). The combination of the liquid prilocaine base or micro rod prilocaine base and the HFC propellants forms a stable liquid solution.

During formulation of a particular prilocaine base/HFC solution, liquid prilocaine was placed in a 4 ounce glass bottle of known weight. The bottle was weighed to determine the weight of liquid prilocaine base. The bottle was then sealed with a continuous valve. HFC-134a was added to the bottle by pressure fill. The bottle was weighed again to determine the weight of HFC-134a added. The bottle was agitated gently to ensure intermingling of the liquid prilocaine base and the HFC. The mixture was found to form a clear and stable solution that did not precipitate out the prilocaine base when left standing or cooled. The valve was opened for short intervals to let out vaporized HFC-134a gas, and the bottle was weighed intermittently. The solution remained clear and stable after each portion of HFC-134a gas was discharged. This process was continued until all vaporizable gas was let out of the bottle. The weight of the bottle after the vaporizable gas had been discharged indicated a 1:1 weight ratio of prilocaine:HFC-134a residue (product remaining in bottle). By leaving the bottle open for twenty-four hours with intermittent weighing, it was determined that the HFC-134a slowly came out of solution until the weight of the bottle indicated the presence of liquid prilocaine base alone. Infra-red spectroscopy confirmed that the recovered liquid prilocaine base was unaltered by the interaction with HFC-134a.

Cooling of a 1:1 mixture of prilocaine:HFC-134a prepared as described above to −82° C. did not result in prilocaine crystallizing out of solution. Instead, the prilocaine:HFC-134a formed a more viscous solution. This result is surprising in view of prilocaine oridinarily having a 38° C. melting point, and the 1:1 solution being highly concentrated, and it further suggests that some form of association or complex (e.g., ionic) between liquid prilocaine base and the HFC is created. Upon rewarming of the viscous oil to room temperature, the prilocaine:HFC-134a remained a liquid. The cooling test described above demonstrates that the liquid prilocaine base can be used in cold-filling operations that are ordinarily used in MDI packaging or the like without adverse consequences.

Seeding of the 1:1 solution with prilocaine base needle crystals resulted in the prilocaine base crystallizing out of solution over several days.

The association of liquid prilocaine base with HFC propellants has been found to allow its use as a solubilizing agent for dissolving and/or dispersing other medicaments within HFC propellants. In particular, prilocaine base can be used as a solubilizing aid for other local anesthetics, most of which are not ordinarily soluble in HFC propellants. For example, prilocaine base can be used in HFC propellants in combination with the anesthetics procaine, cocaine, chloroprocaine, tetracaine, mepivacaine, lidocaine, bupivacaine, etidiocaine, ropivacaine, and benzocaine. Prilocaine may be used in the preparation of HFC aerosol formulations that are used in inhalation (nasal and/or oral), and topical delivery (e.g., skin wounds, hollow viscus and body cavity delivery), and may be used to solubilize, disperse and/or form stable suspensions with other medicaments including, for example, bronchodilators, anti-inflammatories, antitussives, vasoactive drugs, vasoconstrictors, antibiotics, peptides, steroids, enzymes, antihistamines, benzodiazepines, anti-psychotics, sedatives, vitamins, hormones, enzyme and receptor inhibitors and agonists, 5-aminolevulinic acid and similar agents, antiseptics and disinfectants, etc.

Example 2 provides the compositions of several different HFC aerosol formulations which have been prepared. It can be seen that prilocaine base can be used at widely varying concentrations and may range from 1–99% by weight of the aerosol formulation. Most preferably, the liquid prilocaine base will constitute 1–60% by weight of the HFC aerosol formulation. The HFC propellant can constitute 1–99% by weight of the aerosol formulation, and most preferably 60% to 95% by weight of the aerosol formulation.

If an additional medicament is combined with prilocaine and the HFC propellant, it can constitute 0.01–99% by weight of the aerosol formulation, and most preferably 0.01 to 10% by weight of the aerosol formulation.

EXAMPLE 2

Using the same general method of Example 1, the following formulations were prepared and they provided stable solutions.

| Formulation 1 | | |
| --- | --- | --- |
| Prilocaine base | 140 mg | 4.4% w/w |
| Lidocaine base | 1260 mg | 40.0% w/w |
| HFC-134a | 1760 mg | 55.6% w/w |
| Formulation 2 | | |
| Prilocaine base | 340 mg | 15.5% w/w |
| Lidocaine base | 1260 mg | 57.7% w/w |
| HFC-134a | 580 mg | 26.6% w/w |
| Formulation 3 | | |
| Prilocaine base | 520 mg | 34.9% w/w |
| Lidocaine base | 1260 mg | 84.7% w/w |
| HFC-134a | 175 mg | 11.7% w/w |
| Formulation 4 | | |
| Prilocaine base | 411 mg | 33.4% w/w |
| Lidocaine base | 476 mg | 38.6% w/w |
| HFC-134a | 344 mg | 28.0% w/w |

When cooled to −82° C., formulations 1–4 experienced crystal precipitation of the lidocaine base leaving a thick oily solution of prilocaine and HFC-134a. The lidocaine crystals went back into solution upon rewarming. When the bottle was left open for longer than 24 hours, the HFC-134a evaporated and the local anesthetics crystallized when cooled.

| Formulation 5 | | |
| --- | --- | --- |
| Benzocaine base | 322 mg | 3.7% w/w |
| HFC-134a | 8283 mg | no solution |
| Formulation 6 | | |
| Prilocaine base | 184.6 mg | 56.2% w/w |
| Benzocaine base | 12.7 mg | 3.8% w/w |
| HFC-134a | 131.2 mg | 40.0% w/w |
| | | clear solution |
| Formulation 7 | | |
| Bupivacaine base | 30.0 mg | 0.3% w/w |
| HFC-134a | 10000 mg | no solution |

-continued

| Formulation 8 | | |
|---|---|---|
| Bupivacaine base | 166.0 mg | 33.5% w/w |
| Prilocaine base | 176.0 mg | 35.5% w/w |
| HFC-134a | 153.0 mg | 31.0% w/w |
| | | clear solution |

Formulations 4–8 show that ordinarily insoluble anesthetics (e.g., benzocaine and bupivacaine) can be solubilized in HFC propellants when the liquid prilocaine base:HFC-134a solution is used. When cooled to −82° C., the benzocaine and bupivacaine precipitated out of solution. Upon rewarming, the benzocaine and bupivacaine dissolved back into solution.

| Formulation 9 | | |
|---|---|---|
| Tetracaine base | 60 mg | 1.9% w/w |
| HFC-134a | 3000 mg | 98.1% w/w |
| | | clear solution |
| | | maximum solubility of tetracaine |
| Formulation 10 | | |
| Tetracaine base | 150 mg | 5.8% w/w |
| Prilocaine base | 178 mg | 6.9% w/w |
| HFC-134a | 2250 mg | 87.3% w/w |

Formulations 9–10 demonstrate that prilocaine can be used to enhance the solubility of certain medicaments in HFC propellants

| Formulation 11 | | |
|---|---|---|
| Phenylephrine base | 6 mg | 0.12% w/w |
| HFC-134a | 4890 mg | no solution |
| Formulation 12 | | |
| Phenylephrine base | 8 mg | 0.2% w/w |
| Prilocaine base | 993 mg | 24.7% w/w |
| Lidocaine base | 1009 mg | 25.1% w/w |
| HFC-134a | 1110 mg | 50.0% w/w |

The three medicament bases were first heated and dissolved together. This formulation produced a stable suspension of the phenylephrine. No signs of crystal growth were observed.

| Formulation 13 | | |
|---|---|---|
| Phenylephrine base | 3 mg | 0.2% w/w |
| Prilocaine base | 402 mg | 24.7% w/w |
| Bupivacaine base | 409 mg | 25.1% w/w |
| HFC-134a | 814 mg | 50.0% w/w |

This formulation resulted in a stable suspension. Preheating and mixing of the base compounds was not required in this formulation but is recommended as a method of obtaining even particle sizes of phenylephrine in the suspension. Formulations 11–13 demonstrate the utility of prilocaine in acting as a dispersing agent (as opposed to solubilizing agent) in forming a stable suspension of a medicament.

While the invention has been described in terms of its preferred embodiments, those skilled in the art will recognize that the invention can be practiced with modification within the spirit and scope of the appended claims.

We claim:

1. An aerosol composition for delivering topical local anesthetic to a mammal, comprising:

1–99% wt of hydrofluorocarbon propellant selected from the group consisting of 1,1,1,2-tetrafluoroethane and 1,1,1,2,3,3,3-heptafluoropropane and combinations thereof, said hydrofluorocarbon propellant being the sole propellant in said aerosol composition;

1–99% wt prilocaine base solubilized within said hydrofluorocarbon propellant, said prilocaine base and said hydrofluorocarbon propellant forming a solution that is stable at reduced temperature of at least −82° C.; and 0.01–99% wt of a pharmaceutical other than prilocaine solubilized in said hydrofluorocarbon propellant selected from the group consisting of bronchodilators, antiinflammatories, antitussives, vasoactive drugs, vasoconstrictors, antibiotics which are not antiseptics, peptides which are not enzymes, steroids, enzymes, antihistamines, hormones, 5-aminolevulinic acid, antiseptics, disinfectants, procaine, cocaine, chloroprocaine, tetracaine, mepivacaine, lidocaine, bupivacaine, etidocaine, ropivacaine, benzocaine, and phenylephrine.

2. An aerosol composition for delivering topical local anesthetic to a mammal, comprising:

1–99% wt of hydrofluorocarbon propellant selected from the group consisting of 1,1,1,2-tetrafluoroethane and 1,1,1,2,3,3,3-heptafluoropropane and combinations thereof, said hydrofluorocarbon propellant being the sole propellant in said aerosol composition;

1–99% wt prilocaine base solubilized within said hydrofluorocarbon propellant, said prilocaine base and said hydrofluorocarbon propellant forming a solution that is stable at reduced temperature of at least −82° C.

3. A method of solubilizing or suspending medicaments in hydrofluorocarbon propellants to form an aerosol composition for delivery to a mammal, comprising the steps of:

dissolving 1–99 wt % prilocaine base in 1–99% wt of a hydrofluorocarbon propellant selected from the group consisting of 1,1,1,2-tetrafluoroethane and 1,1,1,2,3,3, 3-heptafluoropropane, and combinations thereof, to produce a solution of prilocaine base and hydrofluorocarbon propellant that is stable at a reduced temperature of at least −82° C., said hydrofluorocarbon propellant being the sole propellant in said aerosol composition; and incorporating 0.01–99wt % of a medicament other than prilocaine selected from the group consisting of bronchodilators, antiinflammatories, antitussives, vasoactive drugs, vasoconstrictors, antibiotics which are not antiseptics, peptides which are not enzymes, steroids, enzymes, antihistamines, hormones, 5-aminolevulinic acid, antiseptics, disinfectants, procaine, cocaine, chloroprocaine, tetracaine, mepivacaine, lidocaine, bupivacaine, etidocaine, ropivacaine, benzocaine, and phenylephrine into said solution by a method selected from the group consisting of solubilizing and suspending.

4. The method of claim 3 wherein said dissolving and incorporating steps are performed simultaneously.

5. The aerosol composition of claim 1 wherein said pharmaceutical is a bronchodilator.

6. The aerosol composition of claim 1 wherein said pharmaceutical is an antiinflammatory.

7. The aerosol composition of claim 1 wherein said pharmaceutical is an antitussive.

8. The aerosol composition of claim 1 wherein said pharmaceutical is selected from the group consisting of vasoactive drugs and vasoconstrictors.

9. The aerosol composition of claim 1 wherein said pharmaceutical is an antibiotic.

10. The aerosol composition of claim 1 wherein said pharmaceutical is a peptide.

11. The aerosol composition of claim 1 wherein said pharmaceutical is a steroid.

12. The aerosol composition of claim 1 wherein said pharmaceutical is an enzyme.

13. The aerosol composition of claim 1 wherein said pharmaceutical is an antihistamine.

14. The aerosol composition of claim 1 wherein said pharmaceutical is a hormone.

15. The aerosol composition of claim 1 wherein said pharmaceutical is selected from the group consisting of enzyme and receptor inhibitors and agonists.

16. The aerosol composition of claim 1 wherein said pharmaceutical is 5-aminolevulinic acid.

17. The aerosol composition of claim 1 wherein said pharmaceutical is an antiseptic.

18. The aerosol composition of claim 1 wherein said pharmaceutical is a disinfectant.

19. The aerosol composition of claim 1 wherein said pharmaceutical is procaine.

20. The aerosol composition of claim 1 wherein said pharmaceutical is cocaine.

21. The aerosol composition of claim 1 wherein said pharmaceutical is chloroprocaine.

22. The aerosol composition of claim 1 wherein said pharmaceutical is tetracaine.

23. The aerosol composition of claim 1 wherein said pharmaceutical is mepivacaine.

24. The aerosol composition of claim 1 wherein said pharmaceutical is lidocaine.

25. The aerosol composition of claim 1 wherein said pharmaceutical is bupivacaine.

26. The aerosol composition of claim 1 wherein said pharmaceutical is etidocaine.

27. The aerosol composition of claim 1 wherein said pharmaceutical is ropivacaine.

28. The aerosol composition of claim 1 wherein said pharmaceutical is benzocaine.

29. The aerosol composition of claim 1 wherein said pharmaceutical is phenylephrine.

* * * * *